US012602448B2

(12) United States Patent
Yao et al.

(10) Patent No.: US 12,602,448 B2
(45) Date of Patent: Apr. 14, 2026

(54) PROGRESSIVE NEURAL ORDINARY DIFFERENTIAL EQUATIONS

(71) Applicant: SRI International, Menlo Park, CA (US)

(72) Inventors: Yi Yao, Princeton, NJ (US); Ajay Divakaran, Monmouth Junction, NJ (US); Hammad A. Ayyubi, La Jolla, CA (US)

(73) Assignee: SRI International, Menlo Park, CA (US)

( * ) Notice: Subject to any disclaimer, the term of this patent is extended or adjusted under 35 U.S.C. 154(b) by 850 days.

(21) Appl. No.: 17/304,163

(22) Filed: Jun. 15, 2021

(65) Prior Publication Data

US 2021/0390400 A1 Dec. 16, 2021

Related U.S. Application Data

(60) Provisional application No. 63/039,567, filed on Jun. 16, 2020.

(51) Int. Cl.
| | |
|---|---|
| *G06F 17/13* | (2006.01) |
| *A61M 16/04* | (2006.01) |
| *G06F 18/213* | (2023.01) |
| *G06N 3/08* | (2023.01) |
| *G06V 10/774* | (2022.01) |

(52) U.S. Cl.
CPC ......... *G06F 17/13* (2013.01); *A61M 16/0493* (2014.02); *G06N 3/08* (2013.01); *G06V 10/774* (2022.01); *G06F 18/213* (2023.01)

(58) Field of Classification Search
CPC ......... G06F 17/13; G06F 18/213; G06N 3/08; G06N 3/044; G06N 3/045; G06N 3/084; G06V 10/774
See application file for complete search history.

(56) References Cited

U.S. PATENT DOCUMENTS

2019/0171936 A1* 6/2019 Karras ................... G06N 3/084
2020/0293870 A1* 9/2020 Isikdogan .............. G06V 10/70

OTHER PUBLICATIONS

Chen et al., "Neural Ordinary Differential Equations" (Year: 2018).*
Du et al., "Time Series Forecasting using Sequence-to-Sequence Deep Learning Framework" (Year: 2018).*
Lu et al., "On Training the Recurrent Neural Network Encoder-Decoder for Large Vocabulary End-To-End Speech Recognition" (Year: 2016).*

(Continued)

*Primary Examiner* — Ryan C Vaughn
(74) *Attorney, Agent, or Firm* — Shumaker & Sieffert, P.A.

(57) ABSTRACT

Techniques are described for neural networks based on Progressive Neural ODEs (PODEs). In an example, a method to progressively train a neural ordinary differential equation (NODE) model comprises processing, by a machine learning system executed by a computing system, first training data, the first training data having a first complexity, to perform training of a first layer for the NODE model; and after performing the first training, processing second training data, the second training data having a second complexity that is higher than the first complexity, to perform training of a second layer for the NODE model.

19 Claims, 7 Drawing Sheets

(56) References Cited

OTHER PUBLICATIONS

Gunther et al., "Layer-Parallel Training of Deep Residual Neural Networks" (Year: 2019).*

Kang et al., "Machine Learning: Data Pre-processing" (Year: 2018).*

Elman, "Learning and development in neural networks: the importance of starting small" (Year: 1993).*

Meade el al., "The Numerical Solution of Linear Ordinary Differential Equations by Feedforward Neural Networks" (Year: 1994).*

Rannen et al., "Encoder Based Lifelong Learning" (Year: 2017).*

Jaderberg et al., "Decoupled Neural Interfaces using Synthetic Gradients," in Int'l Conf. Machine Learning 1627-35 (2017). (Year: 2017).*

Ayyubi et al., "Progressive Growing of Neural ODEs," arXiv.org; arXiv:2003.03695v1, Mar. 8, 2020, 6 pp.

Bengio et al., "Curriculum Learning," in Proceedings of the 26th Annual International Conference on Machine Learning(ICML 2009) Montreal, Canada, Jun. 14-18, 2009, 8 pp.

Chen et al., "Neural Ordinary Differential Equations," 32nd Conference on Neural Information Processing Systems(NIPS 2018) Montreal, Canada, Dec. 2-8, 2018, 13 pp.

Chen et al., "Neural Ordinary Differential Equations," arXiv:1806.07366v5, 32nd Conference on Neural Information Processing Systems(NIPS 2018), Dec. 14, 2019, 18 pp.

Elman, "Learning and development in neural networks: The importance of starting small," Cognition 48;1, Jul. 1993, 30 pp.

Gardner, "Exponential smoothing: The state of the art," Journal of Forecasting, vol. 4, No. 1, Jan. 1, 1985, 38 pp.

Karras et al., "Progressive Growing of GANs for Improved Quality, Stability, and Variation," Nov. 3, 2017, 25 pp.

Li et al., "A scalable end-to-end Guassian process adapter for irregularly sampled time series classification," 29th Conference on Neural Information Processing Systems, Barcelona, Spain, Oct. 28, 2016, 11 pp.

Lipton et al., "Modeling Missing Data in Clinical Time Series with RNNs" Proceedings of Machine Learning for Healthcare, vol. 56, Jun. 2016, 17 pp.

Matissen et al., "Teacher-Student Curriculum Learning" arXiv.org; arXiv:1707.00183v2, Deep Reinforcement earning Symposium (NIPS 2017), Long Beach, CA, USA, Nov. 29, 2017, 15 pp.

Mei et al., "The Neural Hawkes Process: A Neural Self-Modulating Multivariate Point Process," arXiv.org; arXiv:1612.09328v1, Dec. 29, 2016, 16 pp.

Rehfeld et al., "Comparison of correlation analysis techniques for irregularly sampled time series," Jun. 23, 2011, pp. 389-404.

Rubanova et al., "Latent ODEs for Irregularly-Sampled Time Series," 33rd Conference on Neural Information Processing Systems (NeurIPS 2019), Vancouver, Canada, Dec. 8-14, 2019, 11 pp.

Scargle, "Studies in Astronomical Time Series Analysis.II. Statistical Aspects of Spectral Anaylsis of Unevenly Spaced Data," The Astrophysical Journal, Dec. 15, 1982, pp. 835-853.

Shukla et al., "Interpolation-Prediction Networks for Irregularly Sampled Time Series," arXiv.org; arXiv:1909.07782v1, Sep. 13, 2019, 14 pp.

Zaremba et al., "Learning to Execute," arXiv.org; arXiv:1410.4615v2, Dec. 21, 2014, 25 pp.

Zhang et al., "Time series forecasting using a hybrid ARIMA and neural network model," Neurocomputing, Jan. 2003, pp. 159-175.

* cited by examiner

PROGRESSIVE NEURAL ORDINARY DIFFERENTIAL EQUATIONS

This application claims the benefit of U.S. Provisional Patent Application No. 63/039,567, filed 16 Jun. 2020, the entire contents of which is incorporated herein by reference.

TECHNICAL FIELD

This disclosure is related to machine learning systems, and more specifically to training and applying neural differential equations.

BACKGROUND

Neural Ordinary Differential Equations (ODEs) are continuous-time models that defines a hidden state h(t) as a solution to the ODE initial-value problem:

$$\frac{dh(t)}{dt} = f_\theta(h(t), t) \text{ where } h(t_0) = h_0$$

The function $f_\theta$ specifies the dynamics of the hidden state using a neural network with parameters $\theta$. That is, a neural ODE is a type of neural network model in which standard layer to layer propagation is generalized to continuous depth models. Rather than modeling $f$ directly, step-wise Resnet updates $f_{t+1}=f_t+g_t$ for a residual block of a recurrent neural network may be modeled through g as Euler updates $$f_{t+1} = f_t + \frac{df}{dt},$$

and the propagation in the network may be considered the one-step discretization of the forward Euler scheme on an ordinary differentiation equation $$\frac{df}{dt} = g.$$

Neural Ordinary Differential Equations are described in Chen et al., "Neural Ordinary Differential Equations," 32$^{nd}$ Conference on Neural Information Processing Systems, Dec. 14, 2019, which is incorporated by reference herein in its entirety.

SUMMARY

This disclosure describes neural networks based on Progressive Neural ODEs (PODEs). Unlike a conventional Neural ODE (or "NODE"), a PODE is trained using a progressive learning strategy in which the training process for a PODE model gradually increases the training data complexity, as well as the network complexity, as training progresses.

The described techniques for training and generating neural networks based on PODEs may provide one or more technical advantages over conventional NODEs. For example, a PODE may improve the analysis and forecasting of time series, particularly irregularly sampled complex time series. Because the techniques train the network to learn low frequency/complexity and easier to learn trends first and then subsequently augment the network and train the augmented network with the high frequency and more complex periodicities/seasonalities and trends, this enables neural networks based on PODEs to gradually learn to predict complex time series curves containing trends and periodicities/seasonalities, which are otherwise difficult for a conventional NODE to learn.

In an example, a computing system is configured to progressively train a neural ordinary differential equation (NODE) model, the computing system comprising a machine learning system; a memory configured to store the NODE model; and processing circuitry coupled to the memory, the processing circuitry and memory configured to execute the machine learning system, wherein the machine learning system is configured to: process first training data, the first training data having a first complexity, to perform training of a first layer for the NODE model; and after performing the first training, process second training data, the second training data having a second complexity that is higher than the first complexity, to perform training of a second layer for the NODE model.

In an example, a method to progressively train a neural ordinary differential equation (NODE) model comprises processing, by a machine learning system executed by a computing system, first training data, the first training data having a first complexity, to perform training of a first layer for the NODE model; and after performing the first training, processing second training data, the second training data having a second complexity that is higher than the first complexity, to perform training of a second layer for the NODE model.

In an example, a non-transitory computer readable medium comprises instructions for causing processing circuitry to execute a machine learning system to progressively train a neural ordinary differential equation (NODE) model by performing operations comprising processing first training data, the first training data having a first complexity, to perform training of a first layer for the NODE model; and after performing the first training, processing second training data, the second training data having a second complexity that is higher than the first complexity, to perform training of a second layer for the NODE model.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
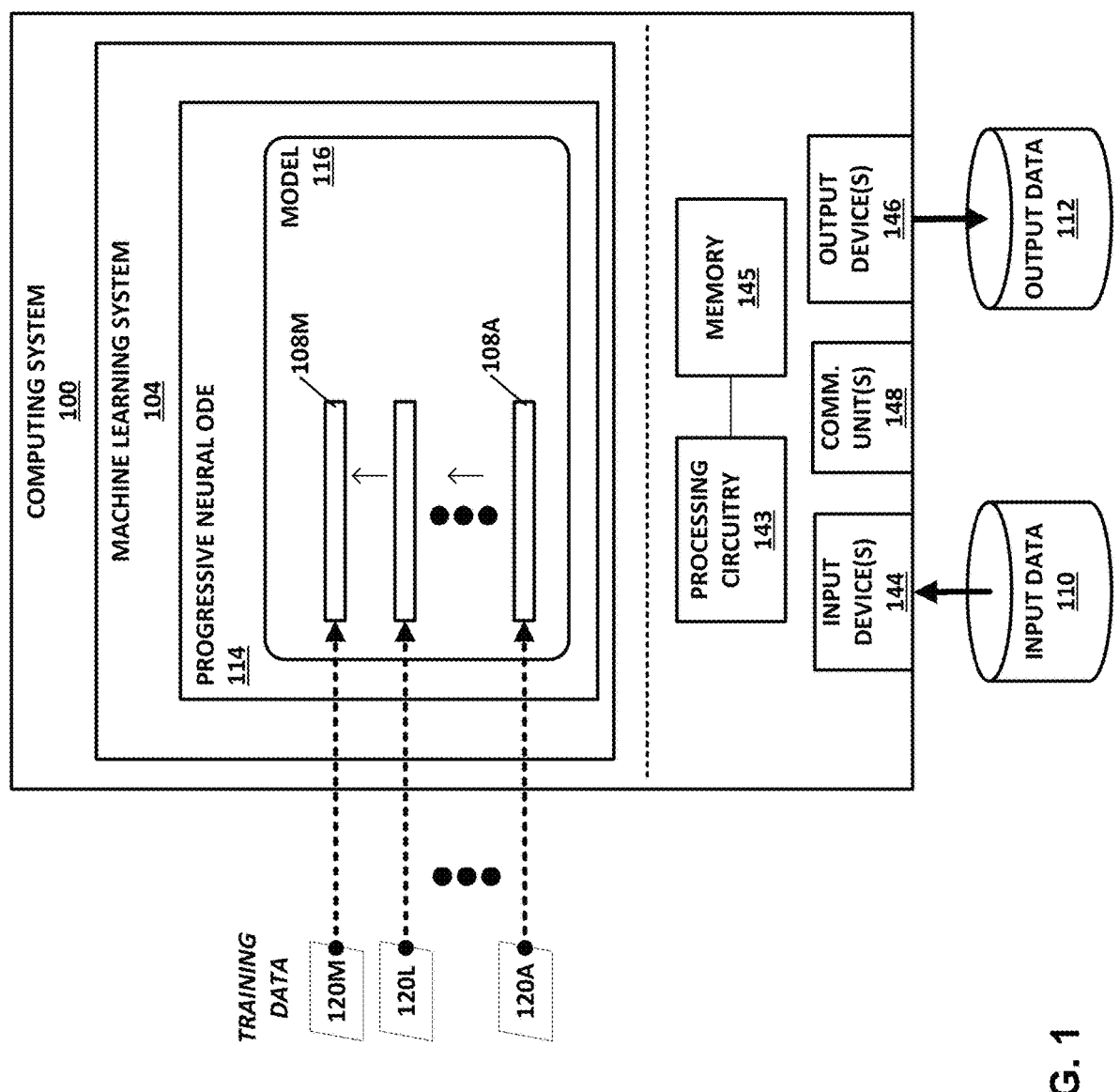
FIG. 1 is a block diagram illustrating an example computing system that implements a machine learning system to train and perform inference using neural networks based on Progressive Neural Ordinary Differential Equations (ODEs), in accordance with the techniques of the disclosure.

FIG. 1 is a block diagram illustrating an example computing system 100 that implements machine learning system 104 to train and perform inference using neural networks based on Progressive Neural Ordinary Differential Equations (ODEs), or "PODEs", in accordance with the techniques of the disclosure. Progressive Neural ODE 114 includes a neural network model 116 ("model 116"), which represents or includes a Neural ODE model. Model 116 is generated by progressively adding and training neural network layers 108A-108M (collectively, "layers 108").

In general, deep learning methods for training neural networks fit a function (typically non-linear) $f$ between input (i) and true output (o) and learn the parameters (weights) w so that the model's output (o') is close to true output (o). The learning part can be posed as an optimization problem, where/is a loss function:

$$\min_w l(o, o'), \text{ s.t. } o' = f(w, i) \tag{1}$$

Model 116 is neural ODE-based (sometimes referred to herein as "NODE"). Model 116 is thus a NODE model. Neural ODE 114 may be an Augmented Neural ODE (ANODE). A residual block $f_t+g_t$ (or "Resnet block") forms residual connections between layers and learns only the residual feature updates $g_t$. In general, a neural ODE is a type of neural network model in which standard layer to layer propagation for layers 108 is generalized to continuous depth models. Rather than modeling f directly, step-wise Resnet updates $f_{t+1}=f_t+g_t$ may be modeled through g as Euler updates $$f_{t+1} = f_t + \frac{df}{dt},$$

and the propagation in the residual network may be considered the one-step discretization of the forward Euler scheme on an ordinary differential equation $$\frac{df}{dt} = g.$$

Model 116 is a model structured according to a NODE architecture and is progressively trained using multiple sets of training data 120A-120M (collectively, "training data 120"). For example, model 116 may be trained as a residual network having respective ODE solver modules in place of residual blocks to determine parameters of model 116. Parameters of a neural network are also known as "weights." An ODE solver computes solutions to ordinary differential equations. The ODE Solver may use, among others, e.g., Runge-Kutta methods, Adams-Bashforth methods, Euler's method, multi-step methods, or Systems of ODEs with absolute converge. A neural ODE may also be referred to as an ODE-net. Backpropagation may be among the methods used to train model 116.

Each of layers 108 may implement a set of transfer functions that are parameterized by a set of parameters (not shown in FIG. 1). As mentioned above, model 116 has a plurality of layers 108. Layers 108 may include an input layer 108A, an output layer 108M, and one or more hidden layers (e.g., layers 108B through 108L). Layers 108 may include and/or implement fully connected layers, convolutional layers, pooling layers, ResNet blocks, ODE transfer functions, and/or other types of layers.

Model 116 may represent or include, for instance, an autoregressive or latent-variable model such as a latent-variable time series model. In a latent-variable time series model, the generative model is defined by an ordinary differential equation for which the initial latent state determines the trajectory. Examples of autoregressive models include recurrent neural networks (RNN) or ODE-RNNs. ODE-RNNs are described in Rubanova et al., "Latent ODEs for Irregularly-Sampled Time Series," 2019, which is incorporated by reference herein in its entirety. In some cases, transformers may be used in place of RNNs/ODE-RNNs.

As further described below with respect to FIG. 2, in some examples, model 116 may implement an encoder-decoder or sequence-to-sequence architecture for encoding variable-length sequences into a fixed-dimensional embedding for processing by the NODE layers, the fixed-dimensional output of which is then decoded into the variable-length sequence. Reference herein to a fixed dimension may refer to a space/manifold of the input and output data, while reference herein to a fixed length may refer to a feature vector; these terms are not mutually exclusive.

Computing system 100 executes machine learning system 104, which may be implemented as software, but may in some examples include any combination of hardware, firmware, and software. Machine learning system 104 trains Progressive Neural ODE 114 and operates Progressive Neural ODE 114 to perform prediction. Computing system 100 may be implemented as any suitable computing system, such as one or more server computers, workstations, mainframes, appliances, cloud computing systems, and/or other computing systems that may be capable of performing operations and/or functions described in accordance with one or more aspects of the present disclosure. In some examples, computing system 100 may represent a cloud computing system, server farm, and/or server cluster (or portion thereof) that provides services to client devices and other devices or systems. In other examples, computing system 100 may represent or be implemented through one or more virtualized compute instances (e.g., virtual machines, containers) of a data center, cloud computing system, server farm, and/or server cluster.

Memory 145 may store information for processing during operation of computing system 100. In some examples, memory 145 may include temporary memories, meaning that a primary purpose of the one or more storage devices is not long-term storage. Memory 145 may be configured for short-term storage of information as volatile memory and therefore not retain stored contents if deactivated. Examples of volatile memories include random access memories (RAM), dynamic random-access memories (DRAM), static random-access memories (SRAM), and other forms of volatile memories known in the art. Memory 145, in some examples, also includes one or more computer-readable storage media. Memory 145 may be configured to store larger amounts of information than volatile memory. Memory 145 may further be configured for long-term storage of information as non-volatile memory space and retain information after activate/off cycles. Examples of non-volatile memories include magnetic hard disks, optical discs, floppy disks, Flash memories, or forms of electrically programmable memories (EPROM) or electrically erasable and programmable (EEPROM) memories. Memory 145 may store program instructions and/or data associated with machine learning system 104 and Progressive Neural ODE 114, described in accordance with one or more aspects of this disclosure.

Processing circuitry 143 and memory 145 may provide an operating environment or platform for computing system 100. Processing circuitry 143 may execute instructions and memory 145 may store instructions and/or data of machine learning system 104 including Progressive Neural ODE 114. The combination of processing circuitry 143 and memory 145 may retrieve, store, and/or execute the instructions and/or data of one or more applications, modules, or software. Processing circuitry 143 and memory 145 may also be operably coupled to one or more other software and/or hardware components, including, but not limited to, one or more of the components illustrated in FIG. 1.

Computing system 100 may perform operations described using software, hardware, firmware, or a mixture of hardware, software, and firmware residing in and/or executing at computing system 100. Computing system 100 may execute machine learning system 104 including Progressive Neural ODE 114 with multiple processors, multiple processing cores, and/or multiple devices (such as in a distributed computing system). Computing system 100 may execute machine learning system 104 including Progressive Neural ODE 114 as one or more virtual machines and/or containers executing on underlying hardware. Machine learning system 104 including Progressive Neural ODE 114 may execute as one or more services of an operating system or computing platform. Machine learning system 104 including Progressive Neural ODE 114 may execute as one or more executable programs at an application layer of a computing platform.

One or more input devices 144 of computing system 100 may generate, receive, or process input. Such input may include input from a keyboard, pointing device, voice responsive system, video camera, biometric detection/response system, button, sensor, mobile device, control pad, microphone, presence-sensitive screen, network, or any other type of device for detecting input from a human or machine.

One or more output devices 146 of computing system 100 may generate, transmit, or process output. Examples of output are tactile, audio, visual, and/or video output. Output devices 146 may include a display, sound card, video graphics adapter card, speaker, presence-sensitive screen, one or more USB interfaces, video and/or audio output interfaces, or any other type of device capable of generating tactile, audio, video, or other output. Output devices 146 may include a display device, which may function as an output device using technologies including liquid crystal displays (LCD), quantum dot display, dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In some examples, computing system 100 may include a presence-sensitive display that may serve as a user interface device that operates both as one or more input devices 144 and one or more output devices 146.

One or more communication units 148 of computing system 100 may communicate with devices external to computing system 100 (or among separate computing devices of computing system 100) by transmitting and/or receiving data, and may operate, in some respects, as both an input device and an output device. In some examples, communication units 148 may communicate with other devices over a network. In other examples, communication units 148 may send and/or receive radio signals on a radio network such as a cellular radio network. Examples of communication units 148 include a network interface card (e.g., an Ethernet card), an optical transceiver, a radio frequency transceiver, a GPS receiver, or any other type of device that can send and/or receive information. Other examples of communication units 148 may include Bluetooth®, GPS, 3G, 4G, and Wi-Fi® radios found in mobile devices as well as Universal Serial Bus (USB) controllers and the like.

Neural Ordinary Differential Equations (NODEs) have proven to be a powerful modeling tool for approximating (interpolation) and forecasting (extrapolation) irregularly sampled time series data. However, NODE performance degrades substantially when applied to real-world data, especially complex data, such as long-term data with complex behaviors (e.g., long-term trend across years, mid-term seasonality/periodicity across months, and short-term local variation across days).

According to techniques of this disclosure, to address the modeling of such complex data with different behaviors at different frequencies (time spans), machine learning system 104 trains model 116 of Progressive Neural ODE 114 using a progressive learning paradigm that the techniques have demonstrated to facilitate training of NODEs for long-term time series forecasting. Specifically, following the principle of curriculum learning, machine learning system 104 trains model 116 by gradually increasing the complexity of training data 120 and by augmenting model 116 capacity as training progresses. This is referred to as progressively training model 116, and therefore model 116 is for a progressively trained (or more simply progressive) neural ODE 114 (that is, Progressive Neural ODE 114). Experiments with both synthetic data and real traffic data demonstrate that the progressive training methodology consistently improves the prediction accuracy performance of Progressive Neural ODE 114 over a typical NODE, at least in some cases by over 64%.

For example, machine learning system 104 obtains training data 120A-120M, where M>1. Training data 120A-120M are ordered by increasing complexity. Training data 120M have higher complexity than training data 120L, and so on, to training data 120B, which have higher complexity than training data 120A. Training data 120A are therefore the simplest training data. In some examples, each of training data 120 is a time series, and the complexity of the training data is a measure of the time series' periodicity, irregularity, and/or trends. For example, higher amplitude or more frequencies in a training data time series will tend to have higher complexity, as will long term trends, as will irregularities in the time series.

In some cases, machine learning system 104 may obtain each of training data 120A-120M from an external source via input devices 144 and/or communication units 148. In some cases, machine learning system 104 or an operator may obtain training data 120M (highest complexity) that is the original time series data and process training data 120M to generate training data 120A-120L. For example, a series of low-pass filters that pass only signals at progressively lower frequencies may be applied to training data 120M to generate training data 120A-120L. For example, training data 120L may represent a time series with only signals having frequencies $<f_L$, training data 120A may represent a time series with only signals having frequencies $<f_A$, where appropriate tuning and low-pass filter settings are used to generate training data 120A-120L. As a result, training data 120A will have the lowest complexity. As another example, principal component analysis (PCA) may be applied to training data 120M to remove differing numbers of components from the training data 120M to generate each of training data 120A-120L.

Machine learning system 104 trains Progressive Neural ODE 114 in multiple steps. Model 116 is initialized with a single layer 108A. Machine learning system 104 processes training data 120A to train the single layer 108A of model 116, which is a NODE model. As such, machine learning system 104 trains the lowest-complexity architecture for model 116 (single layer 108A) with the lowest complexity training data 102A.

At each step thereafter, machine learning system 104 (or an operator) adds a layer to the existing set of previous layers 108. For example, after training initial layer 108A, machine learning system 104 adds layer 108B (not explicitly shown in FIG. 1). Machine learning system 104 then trains model 116, and in particular this additional layer 108B, with training data 120B (not explicitly shown in FIG. 1). At this step, machine learning system 104 may train layers 108A-108B together as part of a single model 116 that remains partial and incomplete. However, in some cases, machine learning system 104 may train additional layer 108B separately from layer 108A during one or more training epochs. At each step, the complexity of training data is thereby increased. "Adding" a layer may involve switching the layer "on", modifying model 116 to include the layer, including the layer in the backpropagation training algorithm, or other technique.

Once machine learning system 104 has trained model 116 with training data 120B, machine learning system 104 performs the next step, which is to add layer 108C (not explicitly shown in FIG. 1). Machine learning system 104 then trains model 116, and in particular this additional layer 108C, with training data 120C (not explicitly shown in FIG. 1). As before, this may include training layers 108A-108C concurrently as part of the same model 116. The steps continue until final layer 108M is added and model 116 of Progressive Neural ODE 114 is trained with training data 120M. As noted above, layer 108M may be an output layer, and training data 120M may be original time series data that have not been simplified to lower-complexity training data 120A-120L.

In some examples, machine learning system 104 may perform alpha blending during addition of new layers and training of model 116. Alpha blending refers to the gradual addition of the new layer 108, the graduality controlled by a configurable parameter a. Alpha blending may reduce instability introduced by adding new, untrained layers during the steps described above.

With Progressive Neural ODE 114 in inference mode, input devices 144 and/or communication units 148 may receive input data 110. Input data 110 may represent observed data that Progressive Neural ODE 114 processes to interpolate input data 110 to generate predictive output data or to extrapolate from input data 110 to generate predictive output data. Machine learning system 104 outputs, via output devices 146, the predictive output data as output data 112 that indicates the predictive output data. Output data 112 may be displayed by output devices 146 and/or stored to a storage device, for instance.

Time series analysis is critical in a number of domains, such as stock prices analysis, logistics, weather analysis, business planning, resource allocation, vehicular and air traffic patterns, oil consumption, seaport activity, etc. Many of these domains produce metrics that are sampled irregularly over time, i.e., not always according to a consistent period (every second, every minute, hourly, daily, and so forth). In addition, metrics from these domains tend to have periodicity, such as weekly traffic patterns, yearly weather patterns, supply and demand cycles, and so forth. Moreover, the metrics from these domains may vary according to long term trends over time frames that exceed the periods of the periodicity of the metrics. As such, the time series data may be both complex and irregularly sampled. Time series data may be based on image data that are preprocessed to generate a scalar or vector from the images. For example, images of a seaport may be preprocessed to identify, for each image, the number of ships in the port in the image. Such images may be irregularly spaced over time due to the nature of the sampling, where satellite coverage is irregular, cloud coverage can prevent sampling at times, and so forth.

Compared with the extensive body of work on time series forecasting of regularly sampled (i.e., equally-spaced) data, fewer methods exist for irregularly sampled (i.e., unevenly-spaced) data. Analysis of such data becomes a critical challenge associated with complex real-world applications such as economics, healthcare, and astronomy, to name a few. One major line of methods transforms irregularly spaced samples into equally spaced ones and then applies existing methods for equally spaced data. For instance, Gaussian Process combined with learned neural networks has been applied for interpolating irregularly sampled data. However, such methods suffer from a number of biases, which significantly degrades the overall performance, especially for highly irregular observations. Classical exponential smoothing methods are applied to irregularly sampled time series mainly for the estimation of trends and seasonalities.

With development in deep learning, learned networks in a data-driven manner (e.g., NODEs) find promising applications to analysis of irregularly sampled data. By applying a progressive learning strategy to training model 116 as described herein, a trained Progressive Neural ODE 114 may improve the analysis and forecasting of time series, particularly irregularly sampled complex real-world time series, such as those with trends and seasonalities, as described above. Because the techniques set forth in this disclosure train the model 116 to learn low frequency/complexity and easier to learn trends first and then subsequently, iteratively augment model 116 with additional layers and train the augmented model 116 with the high frequency and more complex periodicities/seasonalities and trends, this enables neural networks based on PODEs to gradually learn to predict complex time series curves containing trends and periodicities/seasonalities, which are otherwise difficult for a conventional NODE to learn.

Figure 2:
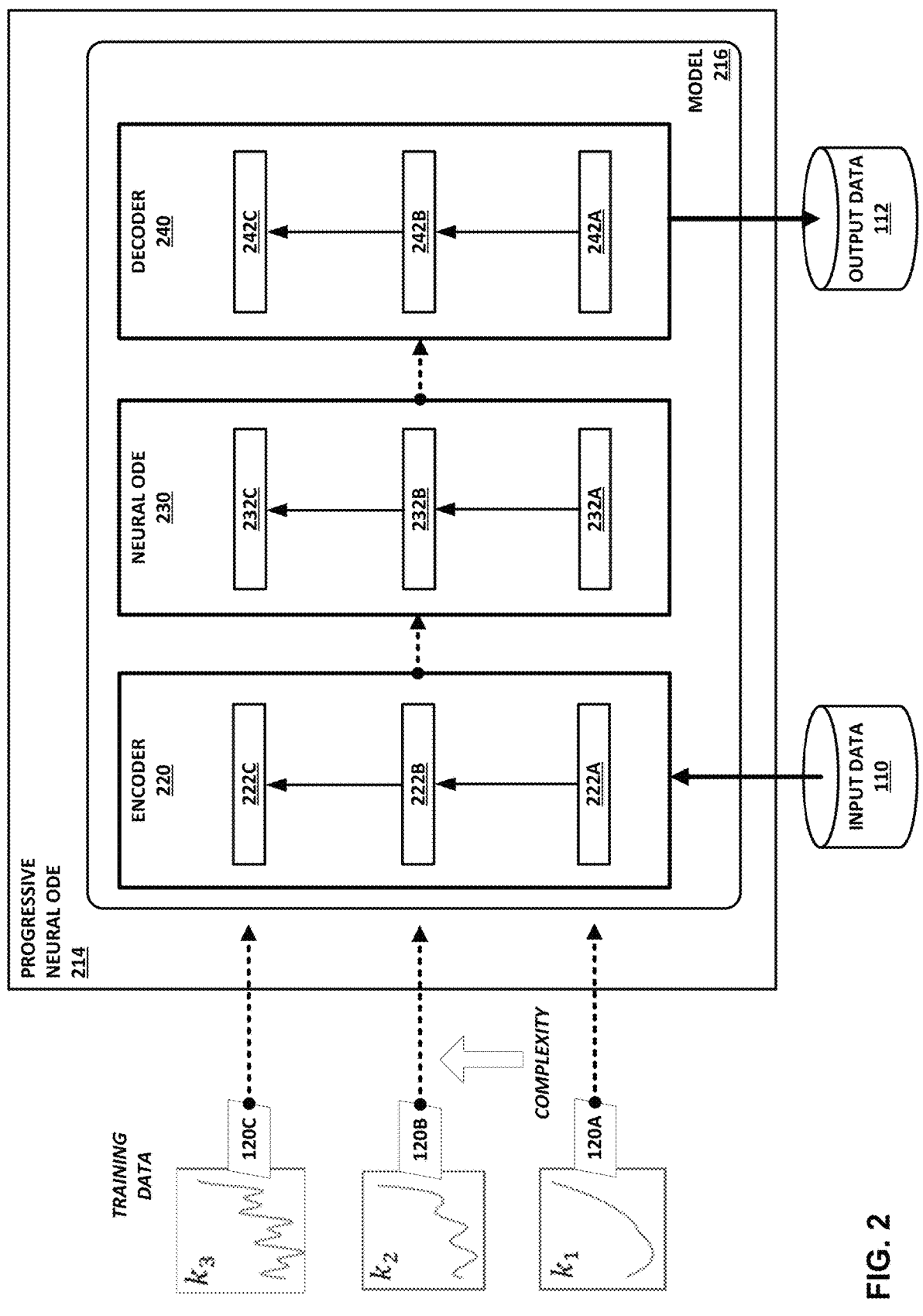
FIG. 2 is a block diagram illustrating, in further detail, a Progressive Neural ODE in accordance with techniques of this disclosure.

FIG. 2 is a block diagram illustrating, in further detail, a Progressive Neural ODE in accordance with techniques of this disclosure. Progressive Neural ODE 214 may represent an example instance of Progressive Neural ODE 114 of FIG. 1.

The model 216 of Progressive Neural ODE 214 includes an encoder 220, a neural ODE (NODE) 230, and a decoder 240. In this example, each of encoder 220, NODE 230, and decoder 240 includes three layers, which are for handling the differing complexities of training data 120A-120C. NODE 230 has layers 232A-232C (collectively, "layers 232"), encoder 220 has layers 222A-222C (collectively, "layers 222"), and decoder has layers 242A-242C (collectively, "layers 242"). Layers 232 of NODE 230 may represent examples of layers 108 of FIG. 1. Alternatively, layers 222, layer 232, and layers 242 may collectively represent examples of layers 108 of FIG. 1. For example, layer 222A and layer 232A and layer 242 may together represent layer 108A. Although only 3 layers are shown in the example of FIG. 2, Progressive Neural ODE 214 may have any number of layers (greater than 1) in various examples. Layers 222 may be alternatively referred to as "encoder layers 222," and layers 242 may be alternatively referred to as "decoder layers 242."

Training data 120A-120C are illustrated graphically in FIG. 2, with higher complexity training data 120C exhibiting one or more frequency signals that are attenuated in training data 120B, which exhibits one or more frequency signals that are attenuated in training data 120A. This illustrates the increase in complexity from training data 120A→training data 120C. However, all of training data 120A-120C illustrate the longer-term trend.

In general, where input data 110 have variable length sequences, encoder 220 maps input data 110 into a fixed length or fixed dimensional embedding that is output to NODE 230. NODE 230 models the temporal dynamics of the input data 110 using irregularly spaced samples and makes a prediction of one or more interpolated or future values (e.g., values for the time series at points in time for which input data 110 has no observed value). Finally, the decoder 240 transforms (e.g., maps) the predicted values, represented in the embedding space, to actual output, an indication of which may be output as output data 112. Output data 112 may thereby have the same dimensions as the input data 110.

Layers of encoder 220, NODE 230, and decoder 240 at the same level are a group of layers. In this example, there are three groups. The first group includes layer 222A, 232A, and 242A. The second group includes layer 222B, 232B, and 242B. And the third group includes layer 222C, 232C, and 242C.

Machine learning system 104 may train each group of layers progressively using training data with gradually increasing complexity. In this way, the techniques involve dividing the complex task of learning functions containing trends and seasonalities into much easier to learn sub-tasks.

Similar to the process of progressively training model 116 described with respect to FIG. 1, training model 216 may be divided into three stages, one for each group of layers. Machine learning system 104 may only train the initial, first group of layers 222A, 232A, and 242A using training data 120A. At the next step, the next, second group of layers 222B, 232B, and 242B may be added to model onto the first group. Machine learning system 104 may train only the first group and the second group using training data 120B, optionally using alpha blending.

In some examples, each of encoder 220 and decoder 240 may represent a neural network, such as a Gated Recurrent Unit, a long short-term memory (LSTM) or other recurrent neural network, a feed forward network, a convolutional neural network (CNN), or other network. NODE 230 is a neural ODE network and, as such, model 216 is NODE-based.

Progressive Neural ODE 214 in this way implements an encoder-decoder or sequence-to-sequence architecture for encoding, by encoder 220, variable-length sequences into a fixed-dimensional embedding for processing by the NODE 230 layers 232A-232C, the fixed-dimensional output of which is then decoded by decoder 240 into the variable-length sequence.

Figure 3:
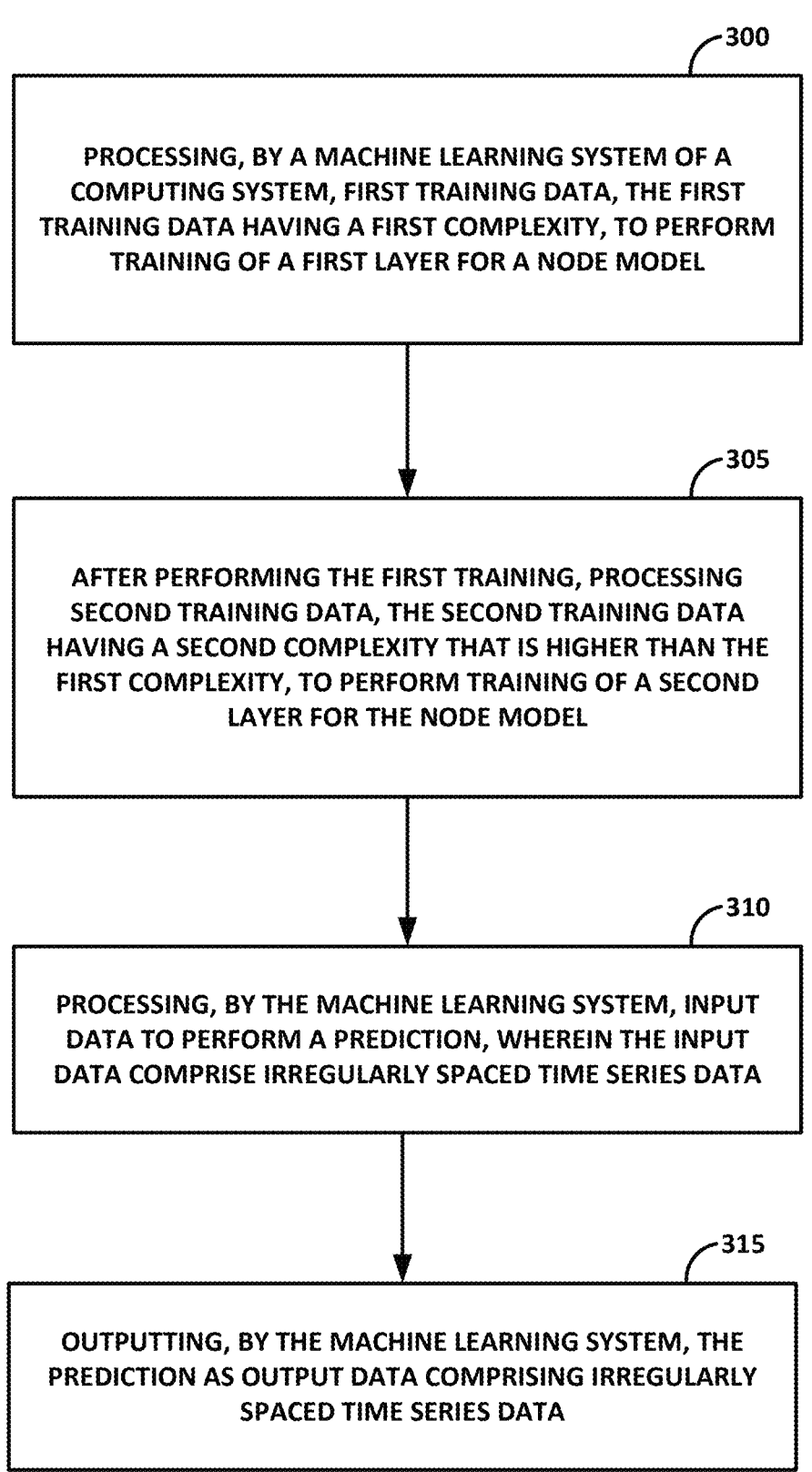
FIG. 3 is a flow diagram illustrating an example mode of operation of a machine learning system, according to techniques of this disclosure.

FIG. 3 is a flow diagram illustrating an example mode of operation of a machine learning system, according to techniques of this disclosure. As part of the training process, machine learning system 104 processes training data 120A having a first complexity to perform first training of first layer 108A for NODE model 116 (300). After performing the first training, machine learning system 104 processes training data 120B having a second complexity—the second complexity higher than the first complexity—to perform second training of second layer 108B for NODE model 116 (305). Second training may also involve training first layer 108A and second layer 108B together during processing of training data 120B. Step 305 may be repeated with additional layers and training data, depending on the number of layers intended for NODE model 116.

After the final layer has been trained with the final set of training data, which may be original time series data unaltered by reducing its complexity, machine learning system 104 is configured to operate NODE model 116 in inference mode. Machine learning system 104 processes input data 110 using NODE model 116 to perform a prediction indicating predicted values (310). The input data 110 may be irregularly spaced time series data, and the predicted values may be values for the function at a particular time for which there is no observed data point. The input data 110 may have at least one of a trend and a periodicity, or simply a periodicity. The periodicity may be one or more signals having respective frequencies. Machine learning system 104 outputs output data 112 having an indication of the prediction (315). In some instances, the output data 112 may be irregularly spaced time series data, which may be generated by decoder 240 as in the example of FIG. 2.

Figure 4:
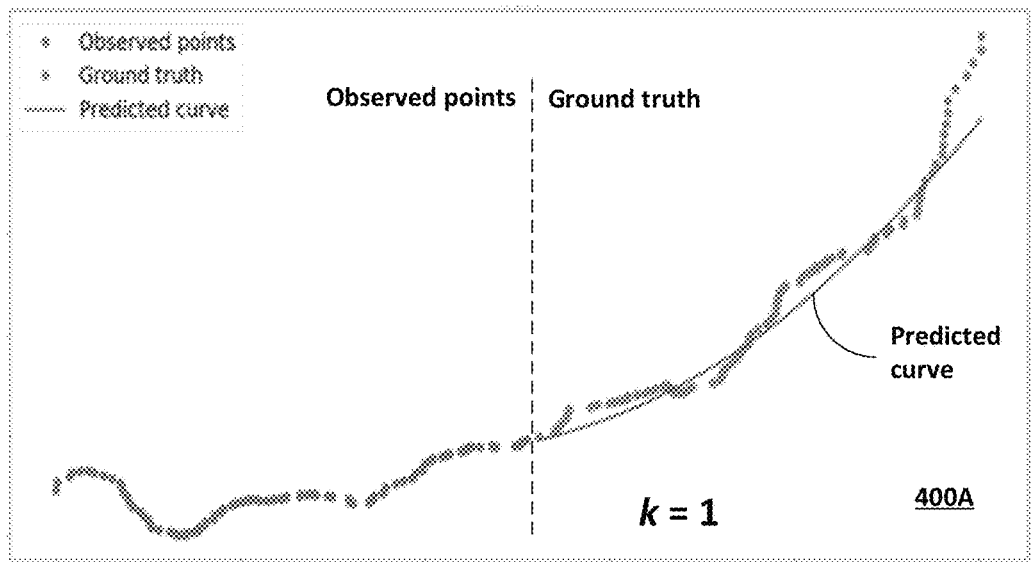
FIGS. 4, 5A-5B, and 6 are plots illustrating test results for forecasting performance of Progressive Neural ODEs.
Figure 4:
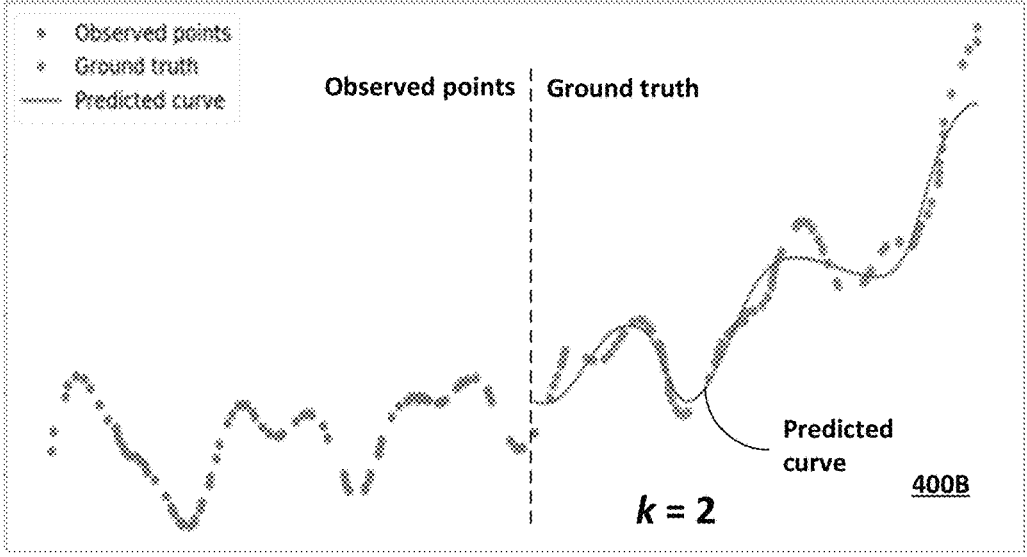
Figure 4:
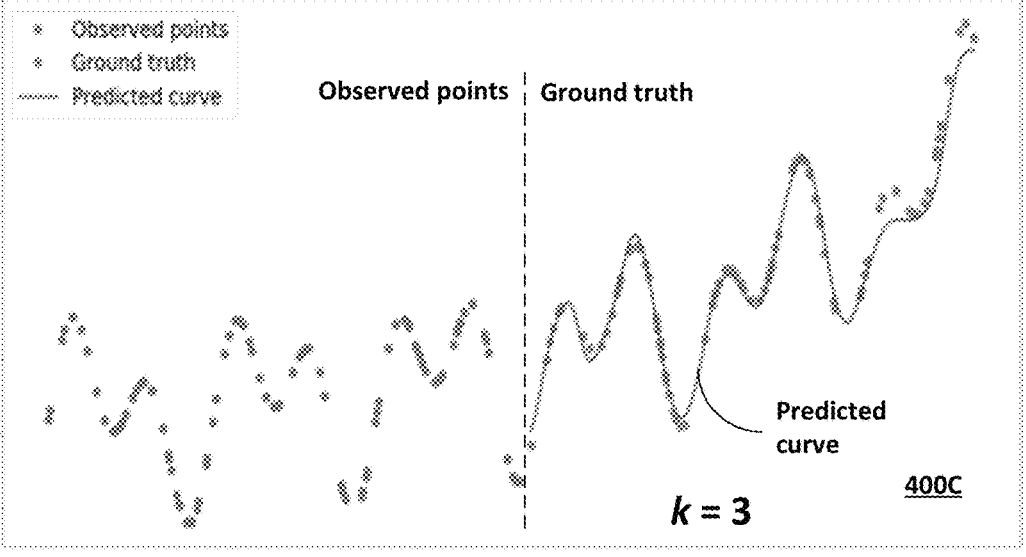

FIGS. 4, 5A-5B, and 6 are plots illustrating test results for forecasting performance of Progressive Neural ODEs. FIG. 4 illustrates forecasting performance after each of multiple different training stages (or "steps") k=1, 2, and 3. Step k=1 may be training initial layer 108A with training data 120A, step k=2 may be adding layer 108B and training layers 108A-108B with training data 120B, and step k=3 may be adding layer 108C and training layers 108A-108C with training data 120C, for instance.

Each plot 400A-400C includes observed points on the left side of the plot and ground truth points on the right side of the plot. Observed points are used as input data, and the illustrated predicted curve depicts a prediction by a neural ODE for extrapolating from the observed points. Ground truth points may be observed points not used as input data but used to evaluate the predicted curve. As can be seen in FIG. 4, the predicted curve fits better after each successive adding/training stages.

Although simulated, aspects of plots 400A-400C may appear similar to training data used to train Progressive Neural ODE and predictions by a Progressive Neural ODE for real-world applications and observed data points. The predictions may be improved relative to those produced by vanilla NODEs, particularly for complex time series data, e.g., time series data having a long-term trend, periodicity/seasonality, and/or irregularly sampled data points. For example, each observed data point may represent a number of ships in a seaport (as in the above example), a temperature, a stock price, a vehicle traffic indicator, or other scalar; and the predicted curve may be used to predict (extrapolate or interpolate) points for use in logistics planning, weather prediction, financial analysis, or other applications such as those listed above.

As one example, machine learning system 104 or an operator may obtain "observed points" as illustrated in plot 400C to be used as training data and, in some cases, may further obtain additional observed points to use as "ground truth" points for prediction testing. The observed points may represent traffic data indicating an amount of vehicle traffic at a location at different times of the day, on different days of the year, or other time scale that has complex traffic patterns exhibiting, for instance, a long-term trend in conjunction with shorter-term seasonality/periodicity.

Progressive Neural ODE 114 may be progressively trained by matching differing complexities of the observed points to layers of model 116. To do this, the observed data points are simplified to create multiple training data sets with differing, reduced layers of complexity. Example processes for reducing complexity of training data are described above. Observed points of plot 400A are lowest complexity and may represent an example of training data 120A. Observed points of plot 400C are highest complexity, may be the original observed points, and may represent an example of training data 120C.

Model 116 is initialized with a single layer 108A. Machine learning system 104 processes observed points shown in plot 400A to train the single layer 108A of model 116. As such, machine learning system 104 training the lowest-complexity architecture for model 116 (single layer 108A) with the lowest complexity training data. After training initial layer 108A, machine learning system 104 adds layer 108B. Machine learning system 104 then trains model 116, and in particular this additional layer 108B, with the observed points shown in plot 400B. Machine learning system 104 then adds layer 108C. Machine learning system 104 then trains model 116, and in particular this additional layer 108C, with the observed points shown in plot 400C. Progressively adding layers 108 to model 116 allows model 116 to be trained with traffic data from which training data exhibiting varying levels of complexity have been derived. By the final step, model 116 is able to effectively predict the complex ground truth points shown in plot 400C.

Figure 5A:
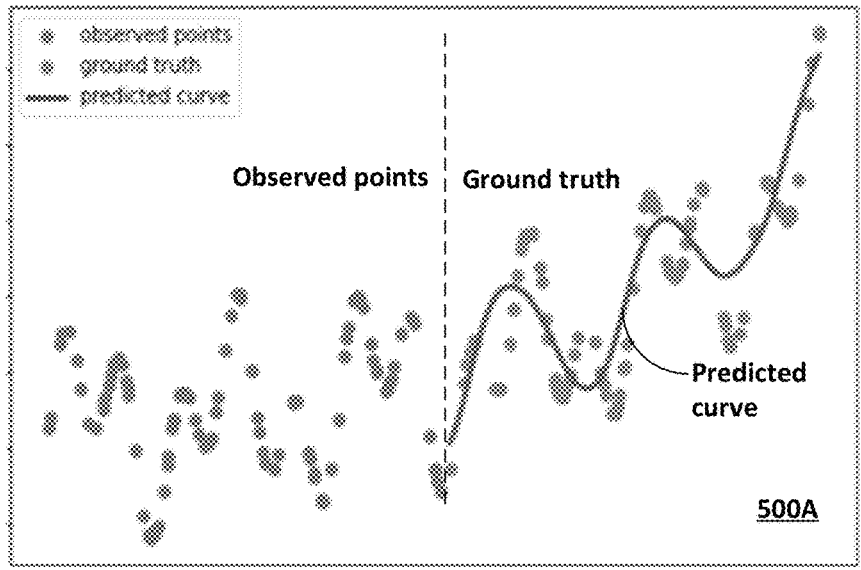
Figure 5A:
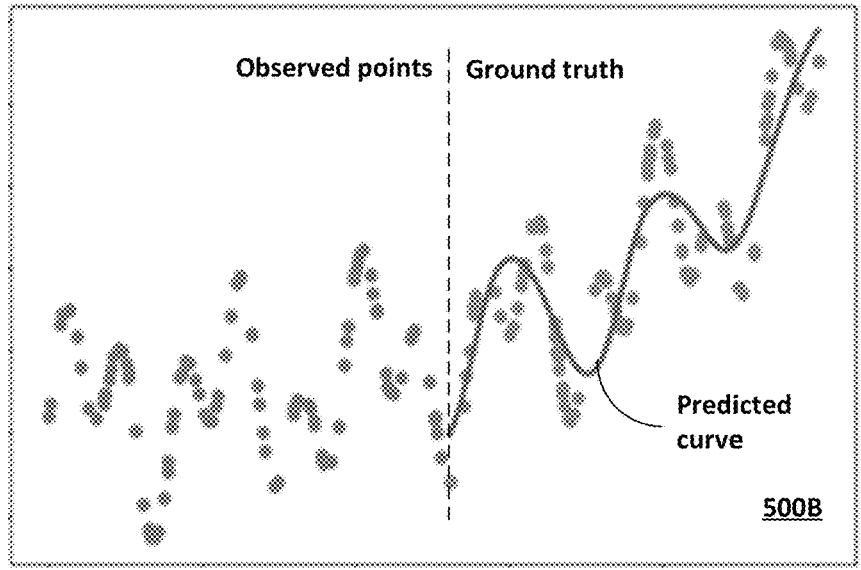
Figure 5A:
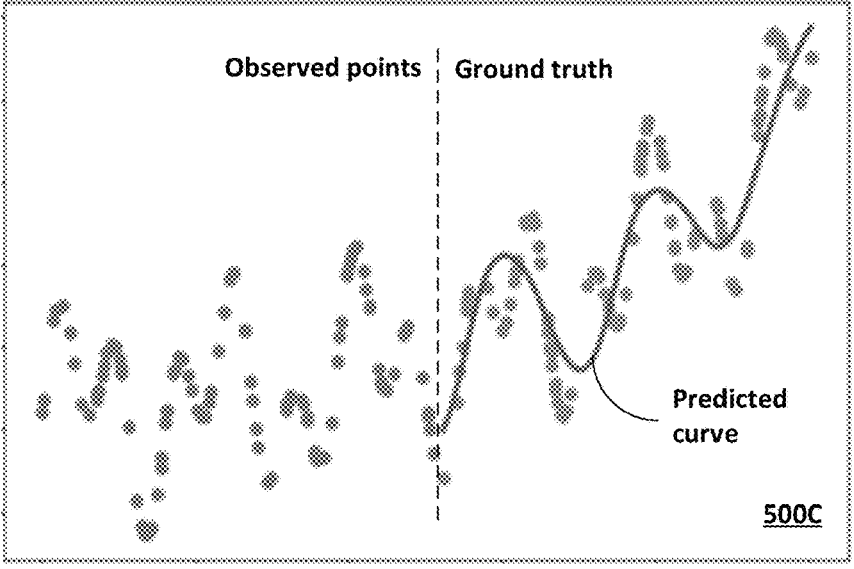
Figure 5B:
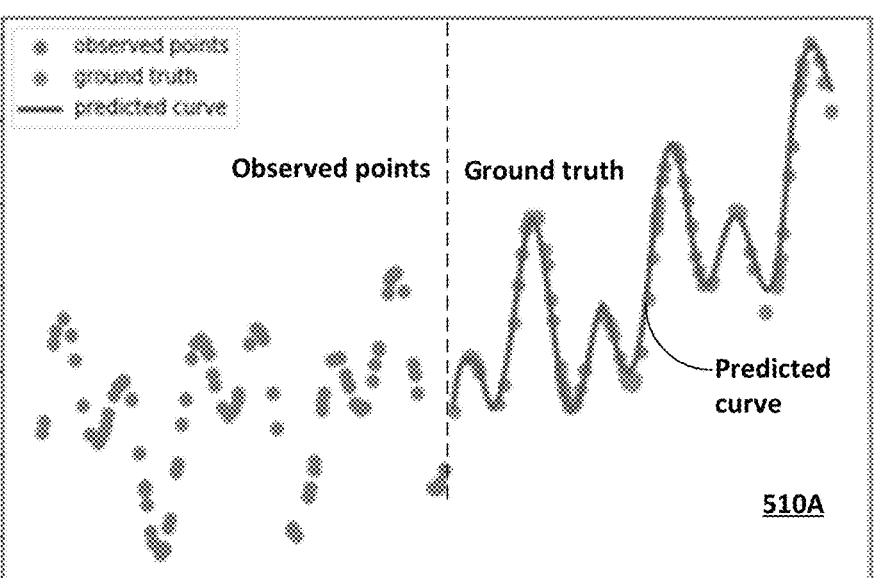
Figure 5B:
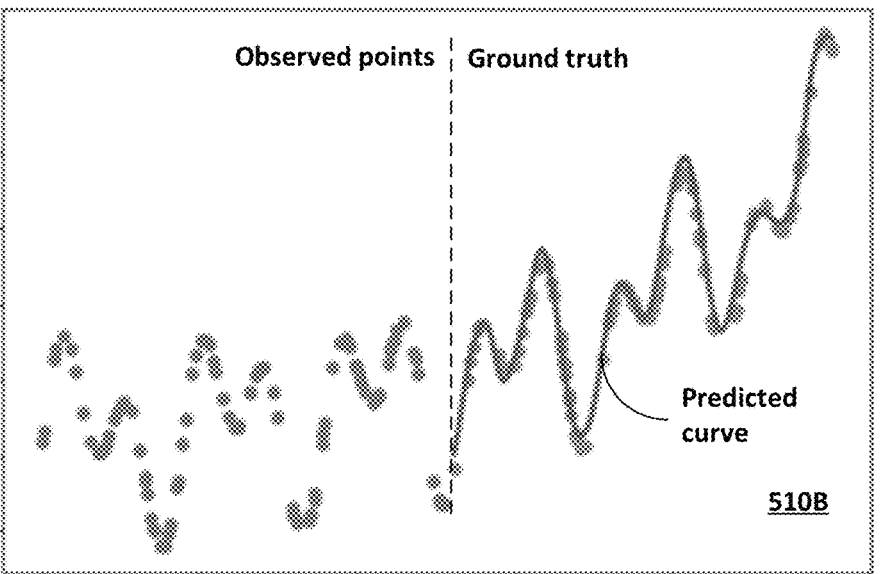
Figure 5B:
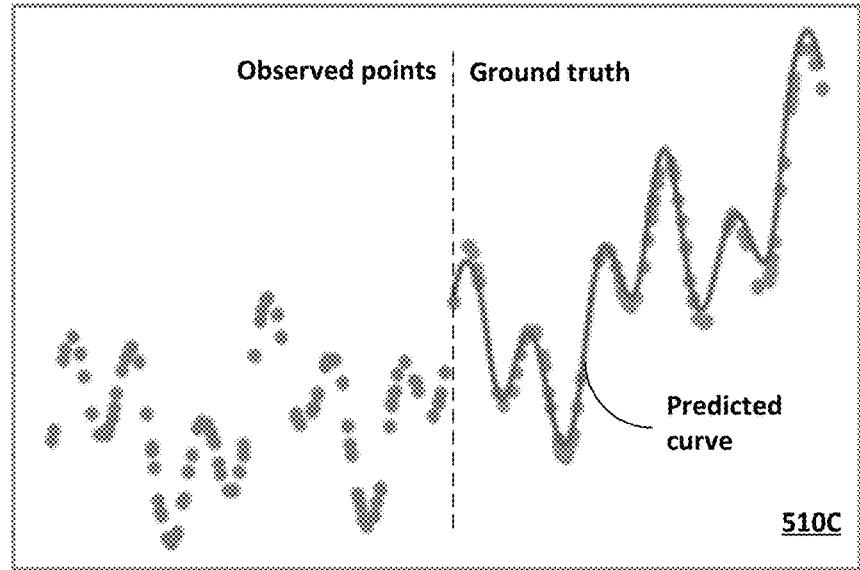

FIG. 5A includes plots 500A-500C and FIG. 5B includes plots 510A-510C with predictions for different input data that is synthetic data generated from the formula:

$$-\exp(cx)+\sin(t_1 x)+\sin(t_2 x) \qquad (2)$$

with each of plots 500A-500C and plots 510A-510C showing samples with different values of c for different trends and different values of $t_1$ and $t_2$ for seasonal fluctuations (periodicity). Plots 500A-500C and plots 510A-510C are lain out similarly to plots 400A-400C. The input data and ground truth for plots 500A and 510A are the same, the input data and ground truth for plots 500B and 510B are the same, and the input data and ground truth for plots 500C and 510C are the same. While plots 500A-500C are generated from input data, ground truth, and predictions made by a conventional/vanilla NODE, plots 510A-510C are generated from input data, ground truth, and predictions made by a Progressive Neural ODE 114 generated according to techniques described in this disclosure. As can be clearly seen, the predicted curves in plots 510A-510C clearly improve upon the predicted curves of plots 500A-500C by more closely fitting the ground truth points. By breaking down the complex curve into simpler curves, the Progressive Neural ODE 114 can learn complex functions incrementally. Conventional NODEs fail to represent the complex dynamics of the synthetic curves, yielding a mean squared error (MSE) of 15.56. In comparison, instances of Progressive Neural ODE 114 are capable of capturing both trend and seasonalities, producing a mean-squared error (MSE) of 0.81, a substantial improvement.

Table 1 compares the MSE of a Progressive Neural ODE 114 against other baselines.

TABLE 1

| MSE on synthetic and PEMS-BAY datasets. | | | | | |
|---|---|---|---|---|---|
| | Models | | | | |
| Dataset | Static | HA | ARIMA | NODE | PODE |
| Synthetic | 36.43 | 35.74 | 29.69 | 15.56 | 0.81 |
| PEMS-BAY (+E03) | 17.58 | 40.45 | 47.78 | 13.80 | 4.87 |

Figure 6:
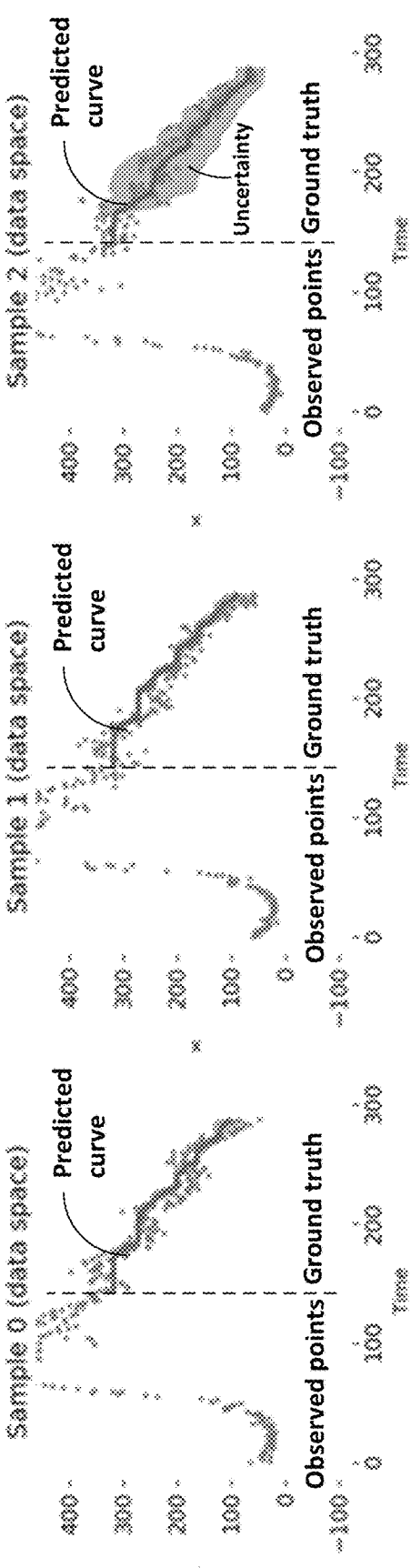

FIG. 6 illustrates forecasting performance by a Progressive Neural ODE 114 on traffic data. Each of the plots shows samples from different sensors and each value is the average vehicles per unit time, aggregated in five minute intervals. This PeMS-BAY ("Performance Measurement System-Bay area") dataset of the samples incorporates both trend and seasonalities (including weekly and daily changes) and, therefore, is commonly used for time series forecasting. The dataset also contains sufficient equally-spaced samples, which allow experiments on the effect of irregular spacing with different sampling strategy (e.g., maximum/minimum spaces).

Each sample is a daily measurement of flow readings. Some of the original dataset may be used for training and some for testing, e.g., an 80%-20% train-test split ratio. In the data for generating the plots of FIG. 6, half of the test points are input to the Progressive Neural ODE, which attempts to predict/forecast the latter half, which are the ground truth. Table 1 shows that PODE improves over NODE by more than 64%. FIG. 6 visualizes the qualitative samples.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A computing system to progressively train a neural ordinary differential equation (NODE) model, the computing system comprising:
   a machine learning system;
   a memory configured to store the NODE model; and
   processing circuitry coupled to the memory, the processing circuitry and the memory configured to execute the machine learning system, wherein the machine learning system is configured to:
      process first training data, the first training data comprising irregularly spaced time series data derived from second training data by applying a complexity-reducing transformation that reduces frequency content of the second training data, to perform training of a first layer for the NODE model, the first layer comprising a first ordinary differential equation (ODE)-based transfer function parameterized by a first set of parameters; and
      after processing the first training data to perform the training of the first layer for the NODE model, process, while retaining the first set of parameters of the first layer fixed, the second training data comprising irregularly spaced time series data to perform training of a second layer for the NODE model, the second layer different from the first layer and comprising a second ODE-based transfer function parameterized by a second set of parameters.

2. The computing system of claim 1, wherein applying the complexity-reducing transformation comprises applying at least one of a low-pass filter or principal component analysis to the second training data.

3. The computing system of claim 1, wherein the machine learning system is configured to:
   process input data to perform a prediction; and
   output the prediction as output data.

4. The computing system of claim 3, wherein the input data comprises irregularly spaced time series data having at least one of a trend and a periodicity.

5. The computing system of claim 3,
   wherein the input data comprises irregularly spaced data, and
   wherein the output data comprises irregularly spaced data.

6. The computing system of claim 1, wherein the irregularly spaced time series data of the first training data and the irregularly spaced time series data of the second training data each has at least one of a trend or a periodicity.

7. The computing system of claim 1, wherein the memory is configured to store an encoder, the encoder configured to:
   map irregularly spaced time series data to fixed length time series data comprising a fixed length embedding; and
   output the fixed length time series data as input data to the NODE model.

8. The computing system of claim 7, wherein the machine learning system is configured to:
   process the first training data to perform training of a first encoder layer of the encoder; and
   after performing the training of the first layer for the NODE model, add a second encoder layer to the encoder and process the second training data to perform training of the second encoder layer of the encoder.

9. The computing system of claim 7, wherein the memory is configured to store a decoder configured to:
   map predicted values output by the NODE model to output data comprising irregularly spaced time series data; and
   output the output data.

10. The computing system of claim 7, wherein the memory is configured to store a decoder configured to:
   map predicted values output by the NODE model to output data comprising irregularly spaced time series data; and
   output the output data, and
   wherein the machine learning system is configured to:
      process the first training data to perform training of a first encoder layer of the encoder and training of a first decoder layer of the decoder; and
      after performing the training of the first layer for the NODE model, add a second encoder layer to the encoder, add a second decoder layer to the decoder, and process the second training data to perform training of the second encoder layer of the encoder and training of the second decoder layer of the decoder.

11. The computing system of claim 1, wherein the NODE model comprises a set of transfer functions that are parameterized by a set of parameters, wherein the set of transfer functions include the first ODE-based transfer function and the second ODE-based transfer function.

12. The computing system of claim 1, wherein the machine learning system is configured to:
   after performing the training of the first layer for the NODE model, add the second layer to the NODE model.

13. The computing system of claim 12, wherein to add the second layer to the NODE model, the machine learning system is configured to:
   apply alpha blending to add the second layer to the NODE model, the alpha blending controlled by a configurable parameter.

14. A method to progressively train a neural ordinary differential equation (NODE) model, the method comprising:
   processing, by a machine learning system executed by a computing system, first training data, the first training data comprising irregularly spaced time series data derived from second training data by applying a complexity-reducing transformation that reduces frequency content of the second training data, to perform training of a first layer for the NODE model, the first layer comprising a first ordinary differential equation (ODE)-based transfer function parameterized by a first set of parameters; and
   after processing the first training data to perform the training of the first layer for the NODE model, processing, while retaining the first set of parameters of the first layer fixed, the second training data comprising irregularly spaced time series data to perform training of a second layer for the NODE model, the second layer different from the first layer and comprising a second ODE-based transfer function parameterized by a second set of parameters.

15. The method of claim 14, further comprising:
   processing irregularly spaced input data to perform a prediction; and
   outputting the prediction as irregularly spaced output data.

16. The method of claim 14, wherein the irregularly spaced time series data of the first training data and the irregularly spaced time series data of the second training data each has at least one of a trend or a periodicity.

17. The method of claim 14, further comprising:

mapping, by an encoder of the machine learning system, irregularly spaced time series data to fixed length time series data comprising a fixed length embedding; and outputting the fixed length time series data as input data to the NODE model.

18. The method of claim 14, further comprising:

after performing the training of the first layer for the NODE model, adding the second layer to the NODE model.

19. Non-transitory computer readable media comprising instructions for causing processing circuitry to execute a machine learning system to progressively train a neural ordinary differential equation (NODE) model, wherein the machine learning system is configured to:

process first training data, the first training data comprising irregularly spaced time series data derived from second training data by applying a complexity-reducing transformation that reduces frequency content of the second training data, to perform training of a first layer for the NODE model, the first layer comprising a first ordinary differential equation (ODE)-based transfer function parameterized by a first set of parameters; and after processing the first training data to perform the training of the first layer for the NODE model, process, while retaining the first set of parameters of the first layer fixed, the second training data comprising irregularly spaced time series data to perform training of a second layer for the NODE model, the second layer different from the first layer and comprising a second ODE-based transfer function parameterized by a second set of parameters.

* * * * *